(12) United States Patent
Takayama et al.

(10) Patent No.: US 12,384,996 B2
(45) Date of Patent: Aug. 12, 2025

(54) CELL CULTURE SYSTEM AND CELL CULTURE METHOD

(71) Applicant: FUJIFILM CORPORATION, Tokyo (JP)

(72) Inventors: Hidetoshi Takayama, Kanagawa (JP); Koju Ito, Kanagawa (JP); Takahiro Oba, Kanagawa (JP); Keisuke Oku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 813 days.

(21) Appl. No.: 17/472,729

(22) Filed: Sep. 13, 2021

(65) Prior Publication Data

US 2021/0403847 A1    Dec. 30, 2021

Related U.S. Application Data

(63) Continuation of application No. PCT/JP2020/007992, filed on Feb. 27, 2020.

(30) Foreign Application Priority Data

Mar. 19, 2019    (JP) .................................. 2019-051925

(51) Int. Cl.
*C12M 1/00*   (2006.01)
*B01L 3/00*   (2006.01)
(Continued)

(52) U.S. Cl.
CPC ....... *C12M 23/58* (2013.01); *B01L 3/502715* (2013.01); *B01L 7/52* (2013.01);
(Continued)

(58) Field of Classification Search
CPC ...... C12M 23/58; C12M 23/16; C12M 23/44; C12M 33/00; C12M 41/44; C12M 41/46;
(Continued)

(56) References Cited

U.S. PATENT DOCUMENTS 5,671,086 A * 9/1997 Parvin .............. G01N 27/44721
                                                           359/398
2013/0004938 A1* 1/2013 Alexandrov ........... C12M 41/48
                                                           435/325
(Continued)

FOREIGN PATENT DOCUMENTS

EP              3192861 A1    7/2017
JP          2016-054724 A    4/2016
(Continued)

OTHER PUBLICATIONS

Alpha Omega Co., "AlphaLab SnR Stimulation and Recording System User's Manual", Version 2.0.3, pp. 12-13 & 52-55, 2013 (Year: 2013).*

(Continued)

*Primary Examiner* — Benjamin R Whatley
*Assistant Examiner* — Curtis A Thompson
(74) *Attorney, Agent, or Firm* — SOLARIS Intellectual Property Group, PLLC

(57) ABSTRACT

A cell culture system includes: a plurality of cell culture channels each of which includes a fluidic device in which cells are cultured, a pump which makes a liquid flow into the fluidic device, a detection unit which detects a state of the cells that are cultured, and a controller which controls the pump and the detection unit; a measurement unit that measures culture environment of the cells which are cultured in the plurality of cell culture channels; and an information processing apparatus that adjusts the culture environment such that an absolute value of a difference between evaluation values for the states of the cells that are cultured in the plurality of cell culture channels is a threshold value or less, on the basis of the state of the cells detected by the detection unit and the culture environment of the cells measured by the measurement unit.

12 Claims, 5 Drawing Sheets

(51) Int. Cl.
  *B01L 7/00* (2006.01)
  *C12M 1/26* (2006.01)
  *C12M 1/34* (2006.01)
  *C12M 1/36* (2006.01)
  *C12M 3/00* (2006.01)
  *C12M 3/06* (2006.01)

(52) U.S. Cl.
  CPC ............ *C12M 23/16* (2013.01); *C12M 23/44* (2013.01); *C12M 33/00* (2013.01); *C12M 41/44* (2013.01); *C12M 41/46* (2013.01); *C12M 41/48* (2013.01); *B01L 2200/027* (2013.01); *B01L 2200/028* (2013.01); *B01L 2200/0621* (2013.01); *B01L 2200/0689* (2013.01); *B01L 2200/147* (2013.01); *B01L 2300/0663* (2013.01)

(58) Field of Classification Search
  CPC ...... C12M 41/48; C12M 41/12; C12M 41/00; C12M 41/36; B01L 3/502715; B01L 7/52; B01L 2200/027; B01L 2200/028; B01L 2200/0621; B01L 2200/0689; B01L 2200/147; B01L 2300/0663; C12N 1/00
  See application file for complete search history.

(56) References Cited

U.S. PATENT DOCUMENTS

| | | | | |
|---|---|---|---|---|
| 2014/0045252 | A1* | 2/2014 | Nakajima | C12M 41/46 435/288.7 |
| 2014/0178996 | A1* | 6/2014 | Shibuya | C12M 27/02 435/287.1 |
| 2014/0322701 | A1* | 10/2014 | Sheth | C12M 41/26 435/5 |
| 2016/0340632 | A1* | 11/2016 | Breinlinger | C12M 41/48 |
| 2017/0166948 | A1 | 6/2017 | Matsumoto | |
| 2017/0241872 | A1* | 8/2017 | Cheung | G01N 33/4833 |
| 2018/0149633 | A1* | 5/2018 | Hasty | C12M 23/16 |
| 2019/0352589 | A1* | 11/2019 | Jing | C12M 41/36 |
| 2019/0358633 | A1* | 11/2019 | Collins | C12M 29/12 |
| 2020/0308523 | A1* | 10/2020 | Murthy | C12M 47/10 |
| 2021/0402399 | A1* | 12/2021 | Sharma | B01L 3/502715 |

FOREIGN PATENT DOCUMENTS

| | | |
|---|---|---|
| JP | 2018-512853 A | 5/2018 |
| WO | 2009/039433 A1 | 3/2009 |
| WO | 2014/018770 A1 | 1/2014 |
| WO | 2014/203322 A1 | 12/2014 |
| WO | 2017/176357 A2 | 10/2017 |
| WO | 2018/098169 A1 | 5/2018 |
| WO | 2018/213357 A1 | 11/2018 |

OTHER PUBLICATIONS

International Search Report issued in International Application No. PCT/JP2020/007992 on May 26, 2020.

Written Opinion of the ISA issued in International Application No. PCT/JP2020/007992 on May 26, 2020.

Extended European Search Report dated Apr. 4, 2022 issued in corresponding EP Patent Application No. 20773129.0.

English language translation of the following: Office action dated Aug. 16, 2022 from the JPO in a Japanese patent application No. 2021-507144 corresponding to the instant patent application.

* cited by examiner

CELL CULTURE SYSTEM AND CELL CULTURE METHOD

CROSS-REFERENCE TO RELATED APPLICATIONS

This application is a continuation application of International Application No. PCT/JP2020/007992, filed Feb. 27, 2020, the disclosure of which is incorporated herein by reference in its entirety. Further, this application claims priority from Japanese Patent Application No. 2019-051925, filed Mar. 19, 2019, the disclosure of which is incorporated herein by reference in its entirety.

TECHNICAL FIELD

The present disclosure relates to a cell culture system and a cell culture method.

RELATED ART

As a technique related to cell culture, a culture station that is used to culture biological cells in a microfluidic device has been known (see JP2018-512853A). The culture station is provided with a pump that makes a culture medium from a culture medium source flow into the microfluidic device and a thermal regulation system that controls the temperature of the microfluidic device.

Incidentally, in the cell culture using a fluidic device, such as a microfluidic device, various functions can be customized through examination of various flow passage structures of the fluidic device. As a result, the fluidic device has been applied to applications such as drug discovery, toxicity evaluation, an organ-on-a-chip, a body-on-a-chip, and analytical chemistry. However, since the fluidic device alone cannot be used for the intended application, a system capable of controlling a liquid feeding system, sensing, adjustment of culture environment, and the like has been required.

Further, in the above-mentioned applications, it is preferable that cell culture using a plurality of fluidic devices can be performed. Furthermore, in this case, it is preferable that the culture environment of each of the plurality of fluidic devices can be adjusted in an integrated manner while referring to the culture state of the cells that are cultured in each of the plurality of fluidic devices. However, the technique described in JP2018-512853A has not considered that the culture environment of each of the plurality of fluidic devices is adjusted in an integrated manner.

SUMMARY

The present disclosure has been made in view of the above circumstances, and an object thereof is to provide a cell culture system and a cell culture method in which the culture environment of each of a plurality of fluidic devices can be adjusted in an integrated manner.

In order to achieve the above-mentioned object, a cell culture system according to the present disclosure includes: a plurality of cell culture channels each of which includes a fluidic device in which cells are cultured, a liquid feeding unit which makes a liquid flow into the fluidic device, a detection unit which detects a state of the cells that are cultured in the fluidic device, and a controller which controls the liquid feeding unit and the detection unit; a measurement unit that measures culture environment of the cells which are cultured in the plurality of cell culture channels; and an integrated controller that adjusts the culture environment such that an absolute value of a difference between evaluation values for the states of the cells that are cultured in the plurality of cell culture channels is a threshold value or less, on the basis of the state of the cells detected by the detection unit and the culture environment of the cells measured by the measurement unit.

Meanwhile, in order to achieve the above-mentioned object, the cell culture method according to the present disclosure using a cell culture system that includes a plurality of cell culture channels each of which includes a fluidic device in which cells are cultured, a liquid feeding unit which makes a liquid flow into the fluidic device, a detection unit which detects a state of the cells that are cultured in the fluidic device, and a controller which controls the liquid feeding unit and the detection unit, the cell culture method includes: measuring culture environment of the cells which are cultured in the plurality of cell culture channels; and adjusting the culture environment such that an absolute value of a difference between evaluation values for the states of the cells that are cultured in the plurality of cell culture channels is a threshold value or less, on the basis of the state of the cells detected by the detection unit and the measured culture environment of the cells.

DETAILED DESCRIPTION

Hereinafter, an exemplary embodiment of the technique according to the present disclosure will be described in detail with reference to the drawings.

Figure 1:
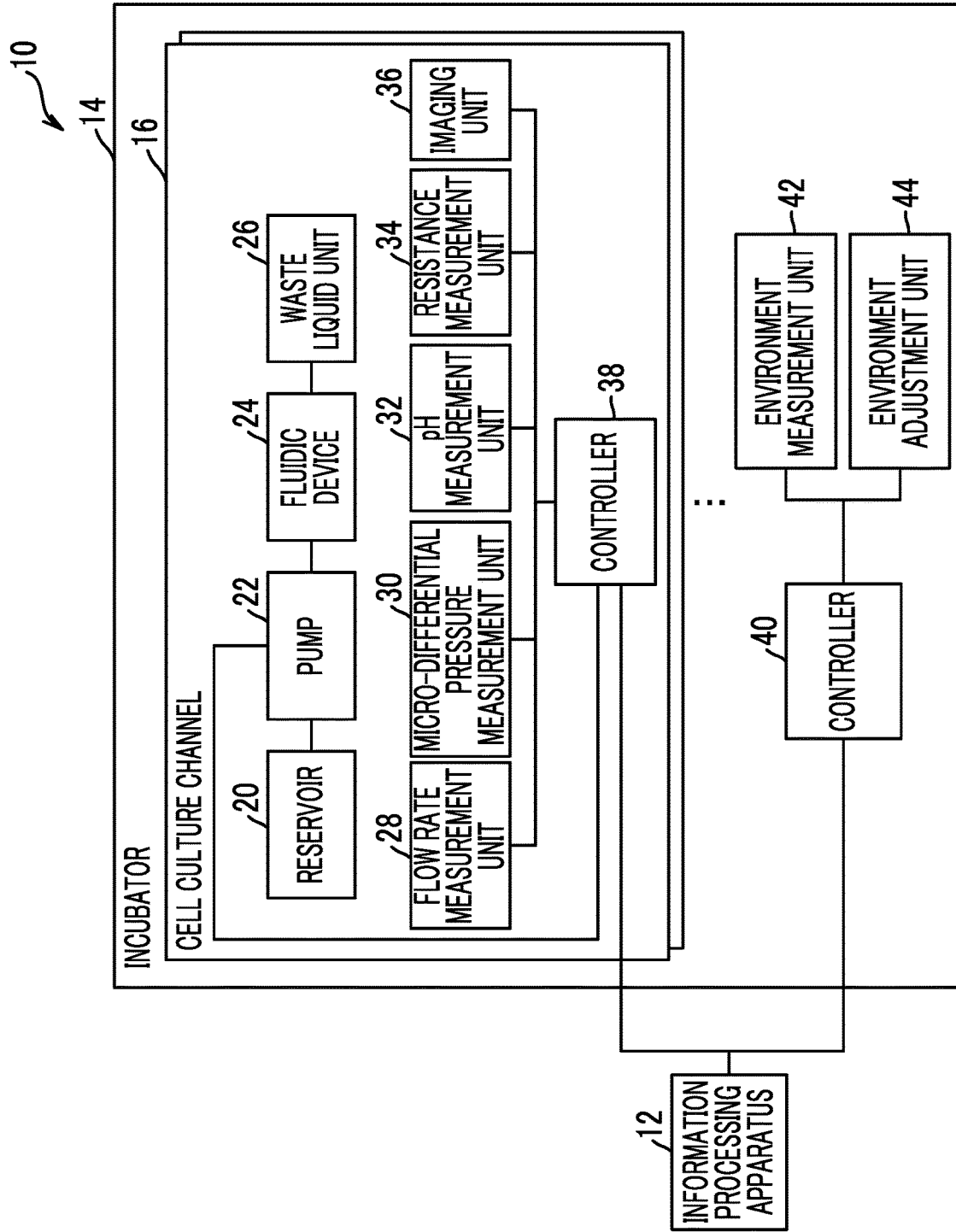
FIG. 1 is a block diagram showing an example of a configuration of a cell culture system according to an embodiment.

First, the configuration of a cell culture system 10 according to the present embodiment will be described with reference to FIG. 1. As shown in FIG. 1, the cell culture system 10 includes an information processing apparatus 12 and an incubator 14. Examples of the information processing apparatus 12 include a personal computer, a server computer, and the like. The cell culture system 10 is used in applications such as drug discovery, toxicity evaluation, an organ-on-a-chip, a body-on-a-chip, and analytical chemistry.

A plurality of cell culture channels 16, a controller 40, an environment measurement unit 42, and an environment adjustment unit 44 are provided inside the incubator 14. The controller 40 is connected to the environment measurement unit 42 and the environment adjustment unit 44. In the present embodiment, an example of an aspect in which the controller 40, the environment measurement unit 42, and the environment adjustment unit 44 are provided in a set inside the incubator 14 will be described, but the present disclosure is not limited thereto. The controller 40, the environment measurement unit 42, and the environment adjustment unit 44 may be provided, for example, in a set for each one cell culture channel 16 or a set for each two cell culture channels 16.

The cell culture channel 16 includes a reservoir 20, a pump 22, a fluidic device 24, a waste liquid unit 26, a flow rate measurement unit 28, a micro-differential pressure measurement unit 30, a potential of hydrogen (pH) measurement unit 32, a resistance measurement unit 34, an imaging unit, 36 and a controller 38. The controller 38 is connected to the pump 22, the flow rate measurement unit 28, the micro-differential pressure measurement unit 30, the pH measurement unit 32, the resistance measurement unit 34, and the imaging unit 36.

A liquid is stored in the reservoir 20. Examples of the liquid stored in the reservoir 20 include a liquid medium, a cell suspension, an added compound solution, an evaluation chemical agent, and a tracer solution. The pump 22 is, for example, a micropump that feeds the liquid by driving a piezo element, and makes the liquid stored in the reservoir 20 flow into the fluidic device 24. The pump 22 is an example of a liquid feeding unit that makes the liquid flow into the fluidic device 24. In the pump 22, the flow rate of the liquid is controlled by the controller 38. In a case where there are a plurality of types of liquids to be fed, the reservoir 20 and the pump 22 are provided in a set for each type of liquid.

In the fluidic device 24, cells are cultured. The fluidic device 24 includes an inlet into which the liquid flows, an outlet out of which the liquid flows, and a flow passage which connects the inlet and the outlet to each other. Examples of the fluidic device 24 include a microfluidic device having micro flow passages. In the following, cells cultured in the fluidic device 24 will be referred to as "cultured cells".

The waste liquid unit 26 discards the liquid flowing out of the fluidic device 24. The cell culture channel 16 may be provided with a circulation unit that circulates the liquid flowing out of the fluidic device 24 to the reservoir 20, instead of the waste liquid unit 26.

The flow rate measurement unit 28 measures the flow rate of the liquid flowing through the fluidic device 24 per unit time and outputs the measurement result to the controller 38. The micro-differential pressure measurement unit 30 measures the micro-differential pressure between the inlet and the outlet of the fluidic device 24 and outputs the measurement result to the controller 38. The pH measurement unit 32 measures the pH of the liquid flowing through the fluidic device 24 and outputs the measurement result to the controller 38. The measurement results of the flow rate measurement unit 28, the micro-differential pressure measurement unit 30, and the pH measurement unit 32 are used, for example, to detect the presence or absence of contamination inside the fluidic device 24.

The resistance measurement unit 34 measures the transepithelial electrical resistance of the cultured cells and outputs the measurement result to the controller 38. The transepithelial electrical resistance is used to evaluate the barrier function of cells, and numerical values thereof vary depending on the environment temperature, the state of cultured cells, and the like. The imaging unit 36 captures an image of the cultured cells in accordance with a predetermined frame rate and outputs image data showing the image obtained by the capturing of the image to the controller 38. The resistance measurement unit 34 and the imaging unit 36 are examples of a detection unit that detects the state of cells. Further, the flow rate measurement unit 28, the micro-differential pressure measurement unit 30, the pH measurement unit 32, the resistance measurement unit 34, and the imaging unit 36 may be formed of various sensors that detect amounts to be measured.

The controller 38 controls the pump 22, the flow rate measurement unit 28, the micro-differential pressure measurement unit 30, the pH measurement unit 32, the resistance measurement unit 34, and the imaging unit 36. Examples of the controller 38 include a processor such as a programmable logic device (PLD).

The controller 40 controls the environment measurement unit 42 and the environment adjustment unit 44. Examples of the controller 40 include a processor such as a PLD. The environment measurement unit 42 measures the culture environment of the cells that are cultured in each cell culture channel 16. The culture environment that is measured by the environment measurement unit 42 includes a temperature of the liquid flowing through the fluidic device 24, an environment temperature around the fluidic device 24, an environment humidity around the fluidic device 24, a carbon dioxide concentration around the fluidic device 24, a nitrogen concentration around the fluidic device 24, and an oxygen concentration around the fluidic device 24. That is, the environment measurement unit 42 includes various sensors capable of measuring the culture environment.

The environment adjustment unit 44 adjusts the culture environment of the cultured cells that are cultured in each cell culture channel 16. The culture environment that can be adjusted by the environment adjustment unit 44 is the same, for example, as the culture environment that can be measured by the environment measurement unit 42. The controller 38 and the controller 40 are connected to the information processing apparatus 12 and are controlled in an integrated manner by the information processing apparatus 12. The environment adjustment unit 44 may adjust the culture environment for each cell culture channel 16. In this case, the environment measurement unit 42 also measures the culture environment for each cell culture channel 16.

Figure 2:
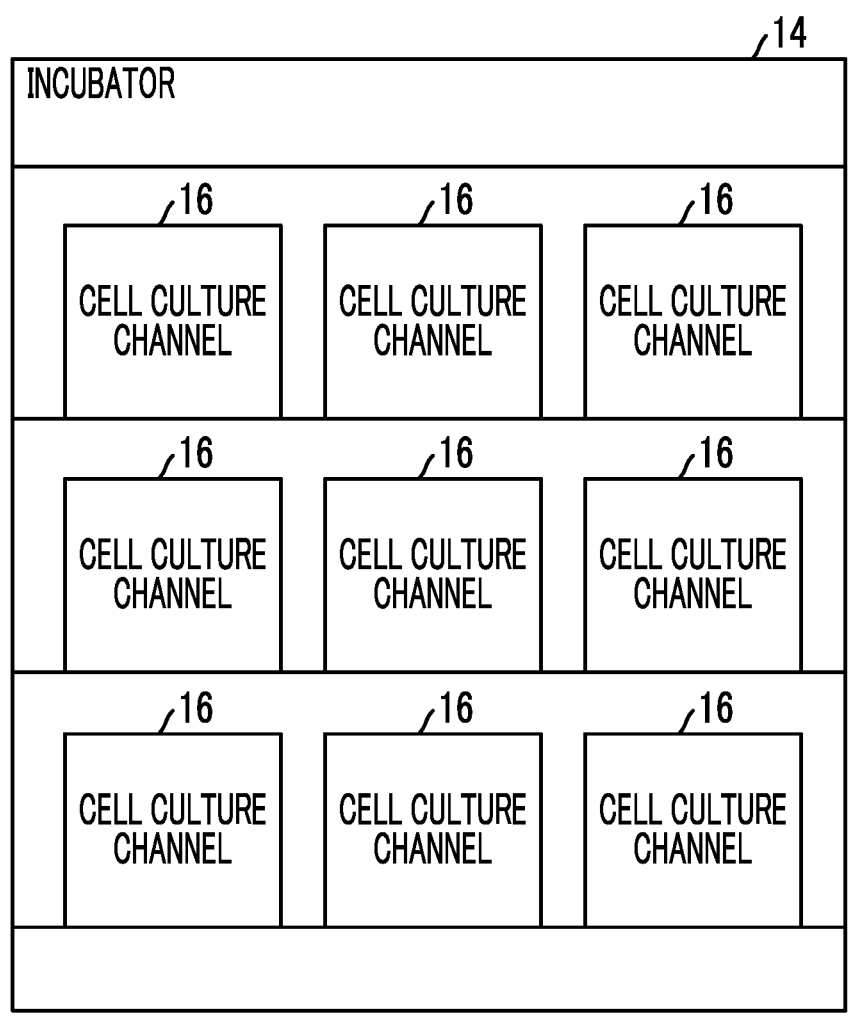
FIG. 2 is a diagram for explaining a disposition state of a cell culture channel according to the embodiment.

The cell culture channels 16 are arranged side by side in the incubator 14 as shown in FIG. 2 as an example. FIG. 2 is a front view of the incubator 14.

Figure 3:
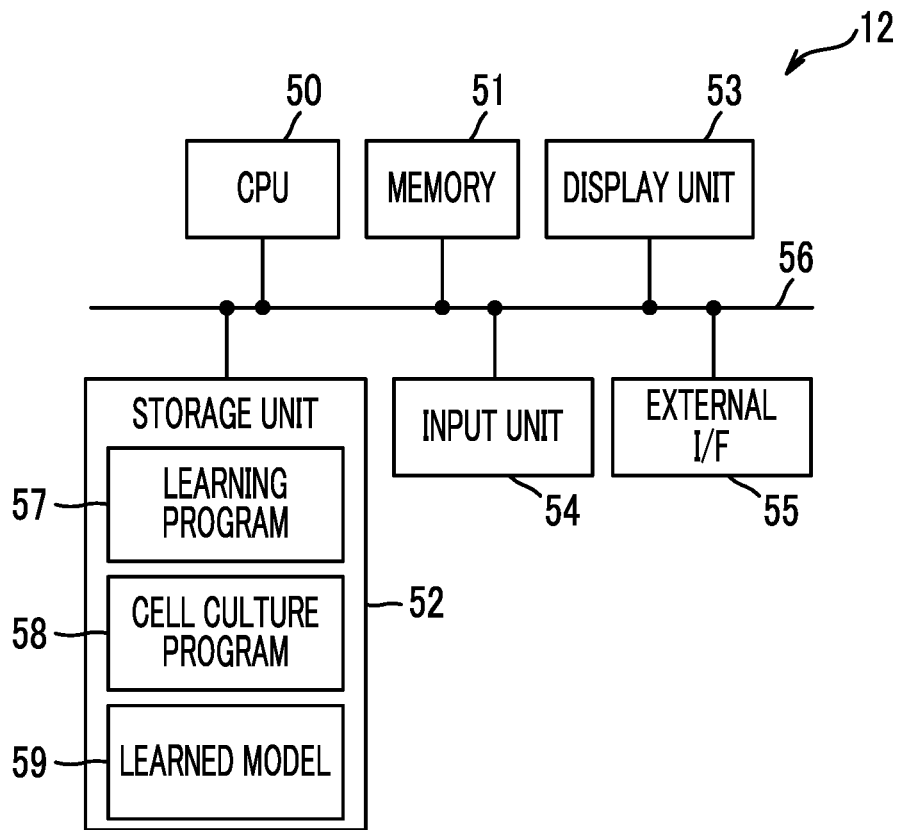
FIG. 3 is a block diagram showing an example of a hardware configuration of an information processing apparatus according to the embodiment.

Next, the hardware configuration of the information processing apparatus 12 according to the present embodiment will be described with reference to FIG. 3. As shown in FIG. 3, the information processing apparatus 12 includes a central processing unit (CPU) 50, a memory 51 as a temporary storage area, and a non-volatile storage unit 52. Further, the information processing apparatus 12 includes a display unit 53, such as a liquid crystal display, an input unit 54, such as a keyboard and a mouse, and an external interface (I/F) 55 to which the controller 38 and the controller 40 are connected. The CPU 50, the memory 51, the storage unit 52, the display unit 53, the input unit 54, and the external I/F 55 are connected to a bus 56.

The storage unit 52 is implemented with a hard disk drive (HDD), a solid state drive (SSD), a flash memory, and the like. A learning program 57, a cell culture program 58, and a learned model 59 are stored in the storage unit 52 as a storage medium. The CPU 50 reads out the learning program 57 and the cell culture program 58 from the storage unit 52, extracts the learning program 57 and the cell culture program 58 to the memory 51, and executes the extracted learning program 57 and cell culture program 58.

<Learning Phase>

Figure 4:
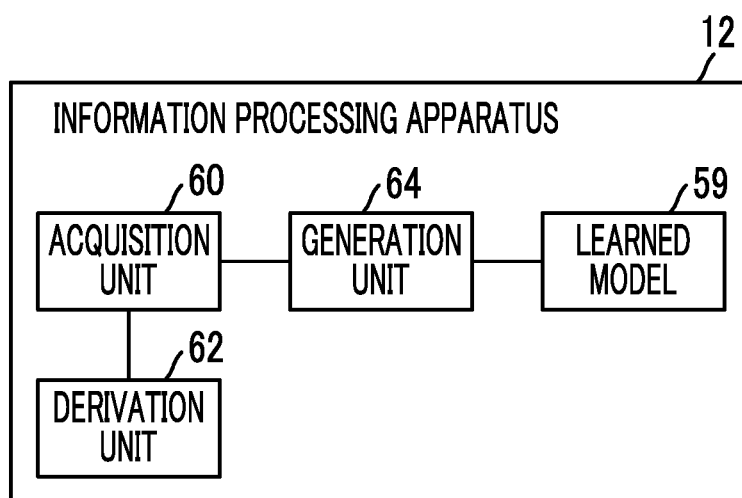
FIG. 4 is a block diagram showing an example of a functional configuration of the information processing apparatus according to the embodiment in a learning phase.

Next, a learning phase for obtaining the learned model 59 will be described. With reference to FIG. 4, a functional configuration of the information processing apparatus 12 according to the present embodiment in the learning phase will be described. As shown in FIG. 4, the information processing apparatus 12 includes an acquisition unit 60, a derivation unit 62, and a generation unit 64. The CPU 50 executes the learning program 57 to function as the acquisition unit 60, the derivation unit 62, and the generation unit 64.

The acquisition unit 60 acquires the transepithelial electrical resistance measured by the resistance measurement unit 34 for each cell culture channel 16, via the controller 38. Further, the acquisition unit 60 acquires image data showing the image of the cultured cells imaged by the imaging unit 36 for each cell culture channel 16, via the controller 38.

In addition, the acquisition unit 60 acquires the evaluation value for the state of the cells that are cultured in the fluidic device 24 of each cell culture channel 16, the culture environment, and information indicating the disposition position of the fluidic device 24 in the incubator 14 (hereinafter, referred to as "a disposition position information").

Specifically, the acquisition unit 60 acquires the flow rate of the liquid flowing through the fluidic device 24 per unit time, which is measured by the flow rate measurement unit 28, as the culture environment of the cultured cells, via the controller 38. Further, the acquisition unit 60 acquires the temperature of the liquid flowing through the fluidic device 24, the environment temperature around the fluidic device 24, the environment humidity around the fluidic device 24, the carbon dioxide concentration around the fluidic device 24, the nitrogen concentration around the fluidic device 24, and the oxygen concentration around the fluidic device 24, which are measured by the environment measurement unit 42, as the culture environment of the cultured cells, via the controller 40.

In addition, the acquisition unit 60 acquires the evaluation value derived by the derivation unit 62, which will be described later, as the evaluation value for the state of the cells. Further, the acquisition unit 60 acquires the disposition position information, for example, from the storage unit 52. The disposition position information of the fluidic device 24 will be described in detail with reference to FIG. 5. For ease of understanding, FIG. 5 shows an example in which the cell culture system 10 is provided with four cell culture channels 16.

Figure 5:
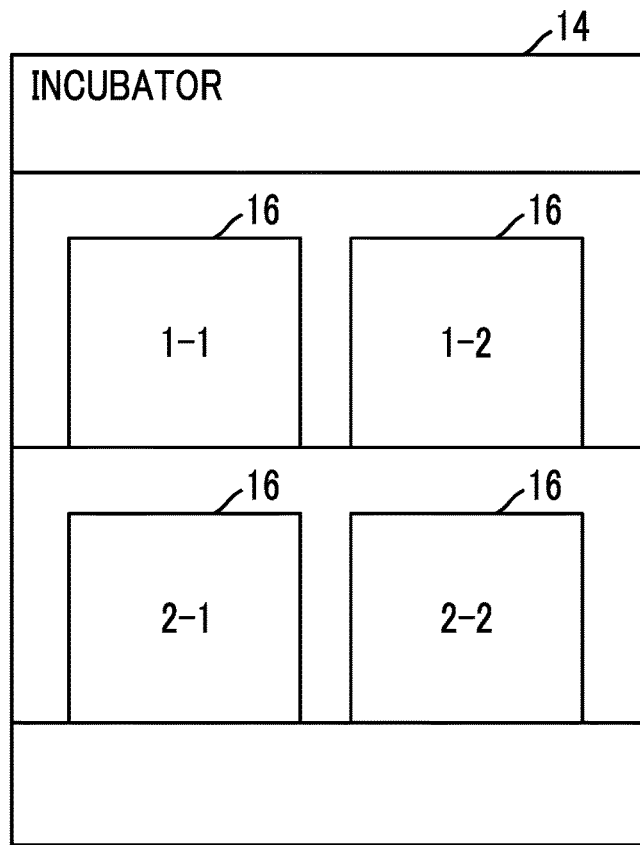
FIG. 5 is a diagram for explaining information representing a disposition position of the cell culture channel according to the embodiment.

As shown in FIG. 5, in the present embodiment, as the disposition position information of the fluidic device 24, information indicating the number from the top and information indicating the number from the left in a case where each cell culture channel 16 is viewed from the front of the incubator 14 are assigned to each cell culture channel 16. For example, "1-1" is assigned as the disposition position information to the cell culture channel 16 which is the first from the top and the first from the left in FIG. 5. In the present embodiment, the disposition position information is associated with the identification information of the cell culture channel 16 and stored in the storage unit 52. The identification information of the cell culture channel 16 is given, for example, in a case where the controller 38 outputs the transepithelial electrical resistance, the image data, and the flow rate acquired for each cell culture channel 16 to the information processing apparatus 12.

Accordingly, in a case where the acquisition unit 60 acquires each information regarding the flow rate of the liquid flowing through the fluidic device 24, the transepithelial electrical resistance, and the image data, via the controller 38, the acquisition unit 60 can specify which cell culture channel 16 each information relates to. Furthermore, the acquisition unit 60 can also specify which cell culture channel 16 disposed at which position in the incubator 14 each information relates to. The acquisition unit 60 periodically acquires various kinds of information described above.

The derivation unit 62 derives the cell directions for the cultured cells of each cell culture channel 16 by using the image shown by the image data of each frame acquired by the acquisition unit 60. The derivation unit 62 can derive the cell direction from the image of each frame by using the directionality of the cells of which the long-axes or short-axes converge into one direction, with respect to the flowing liquid.

Further, the derivation unit 62 derives the cell migration distance from the image of each frame and divides the migration distance by the time between frames to derive the cell migration speed. The cell direction and the cell migration speed are examples of information that is derived from the images obtained by imaging cells. Further, the cell direction, the cell migration speed, and the transepithelial electrical resistance are examples of information representing the state of the cells.

The derivation unit 62 derives an evaluation value for the state of the cells, for the cultured cells of each cell culture channel 16, on the basis of the transepithelial electrical resistance, the cell direction, and the cell migration speed. In the present embodiment, the derivation unit 62 derives a higher evaluation value, for example, as the numerical value, which is set to 10 levels from 1 to 10, increases, as the evaluation value for the state of the cells. The derivation unit 62 may derive a higher evaluation value, for example, as the convergence degree of the cell directions increases. Alternatively, the derivation unit 62 may derive a higher evaluation value, for example, as the cell migration speed increases. Alternatively, the derivation unit 62 may derive a higher evaluation value, for example, as the magnitude of transepithelial electrical resistance increases. In addition, the derivation unit 62 may use the shear stress quantification of the cells to derive the evaluation value for the state of the cells.

For example, the user adjusts the culture environment for each cell culture channel 16 while checking the evaluation value for the state of the cultured cells. With this adjustment, for example, the evaluation values for the states of the cultured cells of the four cell culture channels 16 change. The generation unit 64 according to the present embodiment uses, as training data, the evaluation values before adjustment of the culture environment, the culture environment after the adjustment, and the disposition position information, in a case where, due to the adjustment, each evaluation value becomes a first threshold value or more and the absolute value of the difference in evaluation value between the cell culture channels becomes a second threshold value or less, among the evaluation values for the states of the cells, the culture environment, and the disposition position information. This is because it is preferable that the cells of which the evaluation value is a certain value or more and the variation in state is small can be obtained in each cell culture channel 16.

In a case where a first threshold value is set to 8 and a second threshold value is set to 0, the culture environment after adjustment of the culture environment, the disposition position information, and the evaluation values before the adjustment, for example, when due to the adjustment, the evaluation values for the states of the cultured cells of the four cell culture channels 16 are from 3, 4, 2, 5 to 8, 8, 8, 8, respectively, are used as the training data.

Figure 6:
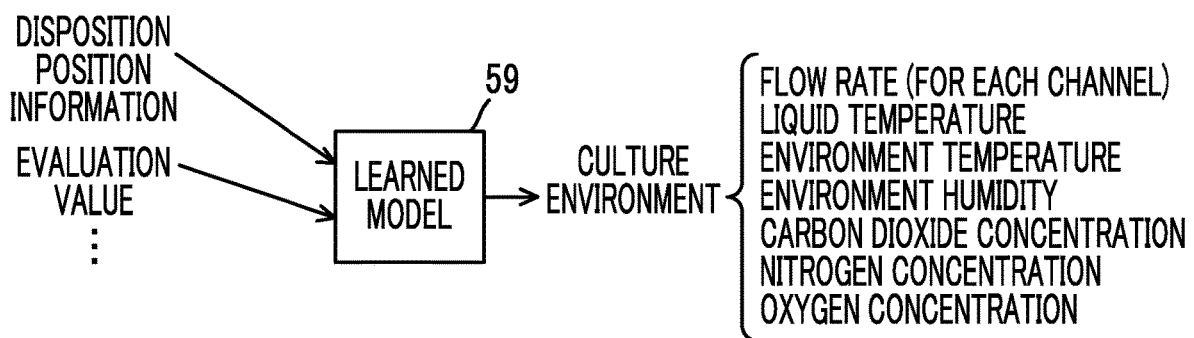
FIG. 6 is a diagram for explaining a learned model according to the embodiment.

The user repeatedly cultures the cells in the cell culture system 10, so that the generation unit 64 can obtain a large number of training data. As shown in FIG. 6 as an example, the generation unit 64 generates the learned model 59 in which the evaluation value and the disposition position information for each cell culture channel 16 are received as an input and the culture environment is output, through the machine learning using the training data obtained as described above. The culture environment that is output by the learned model 59 includes the flow rate of the liquid flowing through the fluidic device 24 per unit time, the temperature of the liquid flowing through the fluidic device 24, the environment temperature around the fluidic device 24, the environment humidity around the fluidic device 24, the carbon dioxide concentration around the fluidic device 24, the nitrogen concentration around the fluidic device 24, and the oxygen concentration around the fluidic device 24. For example, the generation unit 64 applies a deep neural network as the learned model 59 to generate the learned model 59 by using the backpropagation method. The generation unit 64 may use a method other than the neural network, such as linear regression and a decision tree, as the machine learning method.

Figure 7:
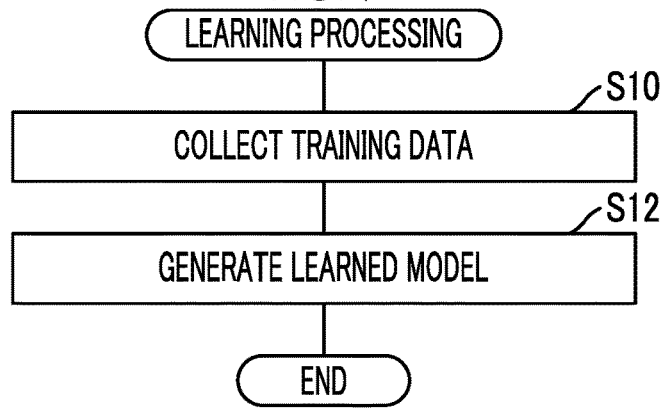
FIG. 7 is a flowchart showing an example of learning processing according to the embodiment.

Next, with reference to FIG. 7, the action of the information processing apparatus 12 according to the present embodiment in the learning phase will be described. The CPU 50 executes the learning program 57, whereby learning processing shown in FIG. 7 is executed. The learning processing shown in FIG. 7 is executed, for example, in a case where the user inputs a start instruction via the input unit 54.

In Step S10 of FIG. 7, the acquisition unit 60 collects training data. As described above, the acquisition unit 60 periodically acquires the evaluation value for the state of the cultured cells, the culture environment, and the disposition position information, for each cell culture channel 16. The acquisition unit 60 collects, as training data, the evaluation values before adjustment of the culture environment, the culture environment after the adjustment, and the disposition position information, in a case where, due to the adjustment, each evaluation value becomes a first threshold value or more and the absolute value of the difference in evaluation value between the cell culture channels becomes a second threshold value or less, among the plurality of evaluation values, the culture environment, and the disposition position information which are acquired.

In Step S12, as described above, the generation unit 64 generates the learned model 59 in which the evaluation value and the disposition position information for each cell culture channel 16 are received as an input and the culture environment is output, through the machine learning using the training data collected by processing of Step S10. When the processing of Step S12 ends, the learning processing ends.

<Operation Phase>

Figure 8:
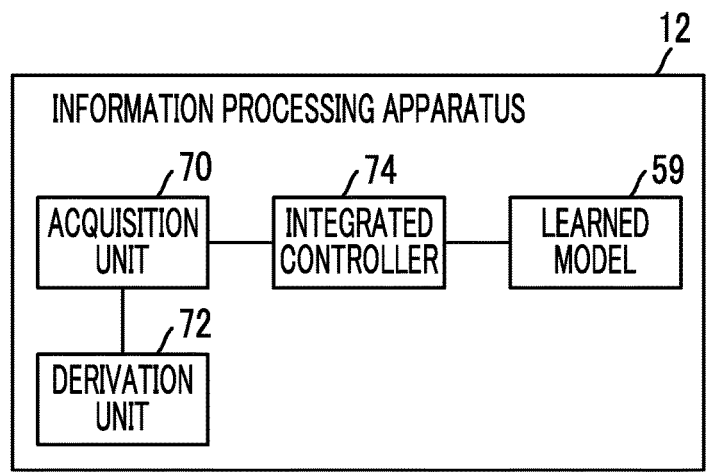
FIG. 8 is a block diagram showing an example of a functional configuration of the information processing apparatus according to the embodiment in an operation phase.

Next, an operation phase using the learned model 59 will be described. The operation phase is a phase in which cells are cultured in each cell culture channel 16. With reference to FIG. 8, a functional configuration of the information processing apparatus 12 according to the present embodiment in the operation phase will be described. As shown in FIG. 8, the information processing apparatus 12 includes an acquisition unit 70, a derivation unit 72, and an integrated controller 74. The CPU 50 executes the cell culture program 58 to function as the acquisition unit 70, the derivation unit 72, and the integrated controller 74.

As in the acquisition unit 60, the acquisition unit 70 acquires transepithelial electrical resistance and image data for each cell culture channel 16. Further, the acquisition unit 70 acquires the evaluation value for the state of the cells that are cultured in the fluidic device 24 of each cell culture channel 16 and the disposition position information of the fluidic device 24, as in the acquisition unit 60.

As in the derivation unit 62, the derivation unit 72 derives the evaluation value for the state of the cells for the cultured cells of each cell culture channel 16.

The integrated controller 74 adjusts the culture environment such that the states of the cultured cells of the cell culture channels 16 are the same, on the basis of the state of the cultured cells and the culture environment of each cell culture channel 16. The integrated controller 74 according to the present embodiment adjusts the culture environment using the learned model 59 described above.

Specifically, the disposition position information and the evaluation value for the state of the cells for each cell culture channel 16, which are acquired by the acquisition unit 70, are received to the learned model 59, as an input, by the integrated controller 74. Further, the integrated controller 74 acquires the culture environment output by the learned model 59 in response to the input.

The integrated controller 74 performs control by outputting the culture environment that can be controlled for each cell culture channel 16 (in the present embodiment, the flow rate), among the acquired the culture environment, to the controller 38. The controller 38 controls the pump 22 such that the flow rate of the liquid flowing through the fluidic device 24 becomes the flow rate received as an input from the integrated controller 74.

The integrated controller 74 performs control by outputting the culture environment that can be controlled for each incubator 14 (in the present embodiment, the culture environment that can be adjusted by the environment adjustment unit 44), among the acquired the culture environment, to the controller 40. The controller 40 controls the environment adjustment unit 44 such that the culture environment that is measured by the environment measurement unit 42 becomes the environment received as an input from the integrated controller 74. That is, the integrated controller 74 adjusts the culture environment such that the absolute value of the difference between the evaluation values for the states of the cells that are cultured in the cell culture channels 16 is the second threshold value or less.

Figure 9:
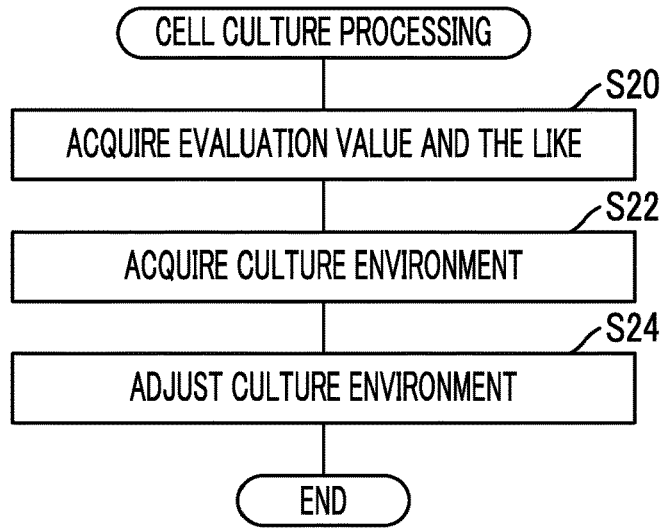
FIG. 9 is a flowchart showing an example of cell culture processing according to the embodiment.

Next, with reference to FIG. 9, the action of the information processing apparatus 12 according to the present embodiment in the operation phase will be described. The CPU 50 executes the cell culture program 58, whereby cell culture processing shown in FIG. 9 is executed. The cell culture processing shown in FIG. 9 is executed, for example, in a case where the user inputs a start instruction via the input unit 54.

In Step S20 of FIG. 9, as described above, the acquisition unit 70 acquires the evaluation value for the state of the cultured cells and the disposition position information for each cell culture channel 16. In Step S22, as described above, the integrated controller 74 acquires the culture environment output by the learned model 59 in response to the input of the evaluation value and the disposition position information received to the learned model 59, which are acquired by the processing of Step S20.

In Step S24, as described above, the integrated controller 74 performs control by outputting the culture environment that can be controlled for each cell culture channel 16, among the culture environment acquired by the processing of Step S22, to the controller 38. Further, the integrated controller 74 performs control by outputting the culture environment that can be controlled for each incubator 14, among the culture environment acquired by the processing of Step S22, to the controller 40. With the processing of Step S24, the culture environment of the cells cultured in each cell culture channel 16 is adjusted. When the processing of Step S24 ends, the cell culture processing ends. The above processing from Steps S20 to S24 is repeated at a predetermined time interval, for example, until the evaluation value for the state of the cultured cells of each cell culture channel 16 is the first threshold value or more and the absolute value of the difference in evaluation value between the cell culture channels is the second threshold value or less. The cells of which the evaluation value is a certain value or more and the variation in state is small, which are obtained by repeating the processing, are used for applications such as drug discovery.

As described above, according to the present embodiment, the culture environment of each of the plurality of fluidic devices 24 can be adjusted in an integrated manner.

In the above-described embodiment, the culture environment that can be adjusted for each incubator 14 by the environment adjustment unit 44 may be individually adjusted for each cell culture channel 16. In this case, an aspect in which the environment measurement unit 42 and the environment adjustment unit 44 are provided in each cell culture channel 16 and controlled by the controller 38 of each cell culture channel 16 is exemplified. Further, in the example of the aspect, the culture environment that is output by the learned model 59 is also output corresponding to each cell culture channel 16. In the example of the aspect, the generation unit 64 may generate the learned model 59 for each cell culture channel 16. Further, in the example of the aspect, the culture environment of each cell culture channel 16 can be individually adjusted by the integrated controller 74.

Further, in the operation phase of the above embodiment, the integrated controller 74 of the information processing apparatus 12 may perform control to make the display unit 53 display the evaluation value for the state of the cultured cells of each cell culture channel 16. In this case, an aspect in which the user switches to a manual operation to adjust the culture environment in a case where the evaluation value for the state of the cells displayed by the display unit 53 does not satisfy the desired condition, is exemplified.

Further, in the above-described embodiment, for example, as a hardware structure of a processing unit that executes various processing such as processing performed by the acquisition units 60 and 70, the derivation units 62 and 72, the generation unit 64, and the integrated controller 74, the following various processors may be used. The various processors include, for example, a programmable logic device (PLD), such as an FPGA, which is a processor having a changeable circuit configuration after manufacture and a dedicated electrical circuit, such as an application specific integrated circuit (ASIC), which is a processor having a dedicated circuit configuration designed to perform specific processing, in addition to the CPU which is a general-purpose processor that executes software (program) to function as various processing units as described above.

One processing unit may be formed by one of the various processors or may be formed by a combination of two or more processors of the same type or different types (for example, a combination of a plurality of FPGAs and a combination of a CPU and an FPGA). Alternatively, the plurality of processing units may be formed by one processor.

A first example of the configuration in which the plurality of processing units are formed by one processor is an aspect in which one or more CPUs and software are combined to form one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system-on-chip (SoC). As described above, as the hardware structure of various processing units, one or more of the various processors are used.

Furthermore, an electrical circuit (circuitry) obtained by combining circuit elements, such as semiconductor elements, may be used as the hardware structure of these various processors.

In the above-described embodiment, the aspect in which the learning program 57 and the cell culture program 58 are stored (installed) in the storage unit 52 in advance has been described, but the present disclosure is not limited thereto. The learning program 57 and the cell culture program 58 may be recorded on a recording medium, such as a compact disc read only memory (CD-ROM), a digital versatile disc read only memory (DVD-ROM), or a universal serial bus (USB) memory, and then provided. Alternatively, the learning program 57 and the cell culture program 58 may be downloaded from an external apparatus via the network.

In the cell culture system according to the present disclosure, the integrated controller may individually adjust the culture environment of the cells which are cultured in the plurality of cell culture channels, for each cell culture channel.

Further, in the cell culture system according to the present disclosure, the integrated controller may adjust the culture environment by using a learned model in which disposition position information representing a disposition position of the cell culture channel and the evaluation value for the state of the cells, which is determined from the state of the cells, are received as an input and the culture environment is output.

In addition, in the cell culture system according to the present disclosure, the state of the cells may include information that is derived from an image obtained by imaging the cells and transepithelial electrical resistance of the cells.

Further, in the cell culture system according to the present disclosure, the culture environment may include a flow rate of the liquid, a temperature of the liquid, an environment temperature around the fluidic device, an environment humidity around the fluidic device, a carbon dioxide concentration around the fluidic device, a nitrogen concentration around the fluidic device, and an oxygen concentration around the fluidic device.

According to the present disclosure, the culture environment of each of the plurality of fluidic devices can be adjusted in an integrated manner.

What is claimed is:

1. A cell culture system comprising:
a plurality of cell culture channels each of which includes a fluidic device in which cells are cultured, a liquid feeding unit which makes a liquid flow into the fluidic device, a first sensor which detects a state of the cells that are cultured in the fluidic device, and a first processor which controls the liquid feeding unit and the first sensor;
a second sensor that measures culture environment of the cells which are cultured in the plurality of cell culture channels; and
a second processor,
wherein the second processor is configured to:
compute evaluation values corresponding to each of the plurality of cell culture channels for the states of the cells that are cultured in each of the plurality of cell culture channels, on the basis of the state of the cells detected by the first sensor and the culture environment of the cells measured by the second sensor;
compute an absolute value of a difference in the evaluation values between different ones of the plurality of cell culture channels; and
adjusts the culture environment such that the computed absolute value is a threshold value or less.

2. The cell culture system according to claim 1, wherein the second processor individually adjusts the culture environment of the cells which are cultured in the plurality of cell culture channels, for each cell culture channel.

3. The cell culture system according to claim 1, wherein the second processor adjusts the culture environment by using a learned model in which disposition position information representing a disposition position of the cell culture channel and the evaluation value for the state of the cells, which is determined from the state of the cells, are received as an input and the culture environment is output.

4. The cell culture system according to claim 2, wherein the second processor adjusts the culture environment by using a learned model in which disposition position information representing a disposition position of the cell culture channel and the evaluation value for the state of the cells, which is determined from the state of the cells, are received as an input and the culture environment is output.

5. The cell culture system according to claim 1, wherein the state of the cells includes information that is derived from an image obtained by imaging the cells and transepithelial electrical resistance of the cells.

6. The cell culture system according to claim 2, wherein the state of the cells includes information that is derived from an image obtained by imaging the cells and transepithelial electrical resistance of the cells.

7. The cell culture system according to claim 3, wherein the state of the cells includes information that is derived from an image obtained by imaging the cells and transepithelial electrical resistance of the cells.

8. The cell culture system according to claim 1, wherein the culture environment includes a flow rate of the liquid, a temperature of the liquid, an environment temperature around the fluidic device, an environment humidity around the fluidic device, a carbon dioxide concentration around the fluidic device, a nitrogen concentration around the fluidic device, and an oxygen concentration around the fluidic device.

9. The cell culture system according to claim 2, wherein the culture environment includes a flow rate of the liquid, a temperature of the liquid, an environment temperature around the fluidic device, an environment humidity around the fluidic device, a carbon dioxide concentration around the fluidic device, a nitrogen concentration around the fluidic device, and an oxygen concentration around the fluidic device.

10. The cell culture system according to claim 3, wherein the culture environment includes a flow rate of the liquid, a temperature of the liquid, an environment temperature around the fluidic device, an environment humidity around the fluidic device, a carbon dioxide concentration around the fluidic device, a nitrogen concentration around the fluidic device, and an oxygen concentration around the fluidic device.

11. The cell culture system according to claim 5, wherein the culture environment includes a flow rate of the liquid, a temperature of the liquid, an environment temperature around the fluidic device, an environment humidity around the fluidic device, a carbon dioxide concentration around the fluidic device, a nitrogen concentration around the fluidic device, and an oxygen concentration around the fluidic device.

12. A cell culture method using a cell culture system that includes a plurality of cell culture channels each of which includes a fluidic device in which cells are cultured, a liquid feeding unit which makes a liquid flow into the fluidic device, a first sensor which detects a state of the cells that are cultured in the fluidic device, a first processor which controls the liquid feeding unit and the first sensor, a second sensor that measures culture environment of the cells which are cultured in the plurality of cell culture channels, and a second processor,
the cell culture method comprising:
by the second processor:
computing evaluation values corresponding to each of the plurality of cell culture channels for the states of the cells that are cultured in each of the plurality of cell culture channels, on the basis of the state of the cells detected by the first sensor and the culture environment of the cells measured by the second sensor;
computing an absolute value of a difference in the evaluation values between different ones of the plurality of cell culture channels; and
adjusting the culture environment such that the computed absolute value is a threshold value or less.

* * * * *